(12) United States Patent
Tang et al.

(10) Patent No.: US 8,445,661 B2
(45) Date of Patent: May 21, 2013

(54) **ISOLATED *STAPHYLOCOCCUS PSEUDOLUGDUNENSIS* POLYNUCLEOTIDES**

(75) Inventors: Yi-Wei Tang, Brentwood, TN (US); Charles W. Stratton, Nashville, TN (US); Jian Han, Huntsville, AL (US)

(73) Assignees: Qiagen Sciences, LLC (DE); Vanderbilt University, Nashville, TN (US)

( * ) Notice: Subject to any disclaimer, the term of this patent is extended or adjusted under 35 U.S.C. 154(b) by 509 days.

(21) Appl. No.: 12/514,268

(22) PCT Filed: Nov. 9, 2007

(86) PCT No.: PCT/US2007/023637
§ 371 (c)(1),
(2), (4) Date: Apr. 30, 2010

(87) PCT Pub. No.: WO2008/143641
PCT Pub. Date: Nov. 27, 2008

(65) Prior Publication Data
US 2010/0240093 A1     Sep. 23, 2010

Related U.S. Application Data

(60) Provisional application No. 60/865,160, filed on Nov. 9, 2006.

(51) Int. Cl.
*C07H 21/02*     (2006.01)
*C07H 21/04*     (2006.01)

(52) U.S. Cl.
USPC .... 536/23.7; 536/23.1; 536/24.32; 536/24.33

(58) Field of Classification Search
None
See application file for complete search history.

(56) References Cited

U.S. PATENT DOCUMENTS 6,380,370 B1 *   4/2002   Doucette-Stamm et al.   536/23.1
6,582,908 B2 *   6/2003   Fodor et al. .................. 506/9

FOREIGN PATENT DOCUMENTS
WO          WO0208266 A2       1/2002

OTHER PUBLICATIONS

NCBI Database (Bethesda, MD, USA) GenBank Accession No. AF298796, Jul. 3, 2001.*
EMBL-EBI Accession No. EMBL: DQ538519. Jun. 14, 2006.*
Layer et al. J Clinical Microbiol. Aug. 2006. 44: 2824-2830.*
DePaulis et al. J Clinical Microbiology. 2003. 41(3): 1219-1224.*
Trulzch, "*Staphylococcus pettenkoferi*" a novel staphylococcal species isolated from clinicial specimens. Diagnostic Microbiology and Infectious Disease 2002, vol. 43, pp. 175-182, p. 177, col. 2, para 2, GenBank accession No. AF322002.

* cited by examiner

*Primary Examiner* — Carla Myers
(74) *Attorney, Agent, or Firm* — Thomas G. Peterson; Nicholas J. Landau; Bradley Arant Boult Cummings LLP

(57) ABSTRACT

Disclosed is an isolated strain of a previously unknown *Staphylococcus, Staphylococcus pseudolugdunensis*. Also disclosed are the sequences of the *S. pseudolugdunensis* tuf gene and 16s rRNA and methods for distinguishing *S. pseudolugdunensis* from other staphylococcal species.

4 Claims, 3 Drawing Sheets

SEQUENCE LISTING

<160> NUMBER OF SEQ ID NOS: 12

<210> SEQ ID NO 1
<211> LENGTH: 1188
<212> TYPE: DNA
<213> ORGANISM: Staphylococcus pseudolugdunensis
<220> FEATURE:
<221> NAME/KEY: gene
<222> LOCATION: (1)..(1188)

<400> SEQUENCE: 1

```
atggctaaag aaaaattcga tcgctcaaaa gaacatgcca atatcggaac tatcggtcac      60
gttgaccatg gtaaaacaac tttaacagct gcaatcgcaa ctgtattagc aaaaaatggt     120
gatactgtag ctcaatctta cgacatgatt gacaacgctc cagaagaaaa agaacgtggt     180
atcacaatca acactgctca catcgagtac caaactgaca aacgtcacta cgctcacgtt     240
gactgcccag acacgctga ctatgttaaa aacatgatca ctggtgcagc tcaaatggac     300
ggcggtatct tagttgtatc tgctgctgac ggtccaatgc cacaaactcg tgaacacatt     360
cttttatcac gtaacgttgg tgtaccagct cttgttgtat tcttaaacaa agttgaccaa     420
```

```
gtagacgacg aagaattatt agaattagtt gaaatggaag ttcgtgactt attaagcgaa      480
tacgacttcc ctggtgacga tgtaccagta atcgctggat ctgcattaaa agcattagaa      540
ggcgacgaag aacaagaaac caaaatctta gaattaatgc aagcagttga cgacttcatc      600
ccaactccag accgtgactc tgacaaacca ttcatgatgc cagttgagga cgtattctca      660
atcactggtc gtggtactgt tgctacaggc cgtgttgaac gtggtcaaat caaagttggt      720
gaagaagttg aaatcatcgg tatggctgat gaatcacaaa aaacaactgt tactggtgta      780
gaaatgttcc gtaagttatt agactacgct gaagctggtg acaacatcgg tgcgttatta      840
cgtggtattg cacgtgaaga cgttcaacgt ggtcaagtat tagctgctcc tggttcaatc      900
acaccacaca ctaaattcaa agctgaagtt tacgtattat ctaaagacga aggtggacgt      960
cacactccat tcttctctaa ctaccgtcca caattctatt tccgtactac tgacgtaact     1020
ggtgtagtta acttaccaga aggtacagaa atggttatgc ctggtgacaa cgttgaaatg     1080
gacgttgaat taatttcacc aatcgctatc gaagacggta ctcgtttctc tatccgtgaa     1140
ggtggacgta ctgtaggatc aggcgttgtt actgaaatct ttgaataa                  1188
```

<210> SEQ ID NO 2
<211> LENGTH: 1556
<212> TYPE: DNA
<213> ORGANISM: Staphylococcus pseudolugdunensis
<220> FEATURE:
<221> NAME/KEY: rRNA
<222> LOCATION: (1)..(1556)

<400> SEQUENCE: 2

```
tttatggaga gtttgatcct ggctcaggat gaacgctggc ggcgtgccta atacatgcaa       60
gtcgagcgaa cagacgggga gcttgctccc ccgacgttag cggcggacgg gtgagtaaca      120
cgtgggtaac ctacctataa gactggaata actccgggaa accggggcta atgccggata      180
acatgttgga ccgcatggtc ctacagtgaa agacggtctt gctgtcactt atagatggac      240
ccgcgccgta ttagctagtt ggtaaggtaa cggcttacca aggcaacgat acgtagccga      300
cctgagaggg tgatcggcca cactggaact gagacacggt ccagactcct acgggaggca      360
gcagtaggga atcttccgca atgggcgaaa gcctgacgga gcaacgccgc gtgagtgatg      420 aaggcctttcg ggtcgtaaaa ctctgttatt agggaagaac aaatgtgtaa gtaactatgc      480
acgtcttgac ggtacctaat cagaaagcca cggctaacta cgtgccagca gccgcggtaa      540
tamgtaggtg gcaagcgtta ccggaattat tgggcgtaa agcgcgcgta ggcggttttct      600 taagtctgat gtgaaagccc acggctcaac cgtggagggy cattggaaac tgggaaactt      660
gagtgcagga ggaaaagtg gaattccatg tgtagcggtg aaatgcgcag agatatggag      720
gaacaccagt ggcgaaggcg actttctggt ctgyaactga cgctgatgtg cgaaagcgtg      780
gggatcaaac aggattagat accctggtag tccacgccgt aaacgatgag tgctaagtgt      840 taggggggttt ccgcccctta gtgctgcagc taacgcatta agcactccgc ctggggagta      900
cgaccgcaag gttgaaactc aaaggaattg acgggaccc gcacaagcgg tggagcatgt      960
ggtttaattc gaagcaacgc gaagaacctt accaaatctt gacatccttt gccccctcta     1020
gagatagagg tttcccccttc gggggacaaa gtgacaggtg gtgcatggtt gtcgtcagct     1080
cgtgtcgtga gatgttgggt taagtcccgc aacgagcgca acccttaagc ttagttgcca     1140
tcattcagtt gggcactcta agttgactgc cggtgacaaa ccggaggaag gtggggatga     1200
cgtcaaatca tcatgcccct tatgatttgg gctacacacg tgctacaatg gacaatacaa     1260
agggcagcta aaccgcgagg tcaagcaaat cccataaagt tgttctcagt tcggattgta     1320
```

```
gtctgcaact cgactacatg aagctggaat cgctagtaat cgtagatcag catgctacgg    1380
tgaatacgtt cccgggtctt gtacacaccg cccgtcacac cacgagagtt tgtaacaccc    1440
gaagccggtg gagcaaccac tttgtggagc tagccgtcga aggtgggaca aatgattggg    1500
gtgaagtcgt aacaaggtag ccgtatcgga aggtgcggct ggaccacctc ctttct        1556
```

```
<210> SEQ ID NO 3
<211> LENGTH: 23
<212> TYPE: DNA
<213> ORGANISM: Artificial
<220> FEATURE:
<223> OTHER INFORMATION: primer sequence to 16S RNA

<400> SEQUENCE: 3
tggagagttt gatcctggct cag                                            23

<210> SEQ ID NO 4
<211> LENGTH: 20
<212> TYPE: DNA
<213> ORGANISM: Artificial
<220> FEATURE:
<223> OTHER INFORMATION: primer sequence for 16S RNA

<400> SEQUENCE: 4
aaggaggtga tccarccgca                                                20

<210> SEQ ID NO 5
<211> LENGTH: 24
<212> TYPE: DNA
<213> ORGANISM: Artificial
<220> FEATURE:
<223> OTHER INFORMATION: primer for tuf gene

<400> SEQUENCE: 5
taagaatagg agagatttwa taat                                           24

<210> SEQ ID NO 6
<211> LENGTH: 21
<212> TYPE: DNA
<213> ORGANISM: Artificial
<220> FEATURE:
<223> OTHER INFORMATION: primer sequence for tuf gene

<400> SEQUENCE: 6
aaattattca aagattwcwg t                                              21

<210> SEQ ID NO 7
<211> LENGTH: 24
<212> TYPE: DNA
<213> ORGANISM: Artificial
<220> FEATURE:
<223> OTHER INFORMATION: internal primer for tuf gene

<400> SEQUENCE: 7
agaataggag agatttwata atgg                                           24

<210> SEQ ID NO 8
<211> LENGTH: 20
<212> TYPE: DNA
<213> ORGANISM: Artificial
<220> FEATURE:
<223> OTHER INFORMATION: internal primer for tuf gene

<400> SEQUENCE: 8
tctgacaaac cattcatgat                                                20
```

```
<210> SEQ ID NO 9
<211> LENGTH: 19
<212> TYPE: DNA
<213> ORGANISM: Artificial
<220> FEATURE:
<223> OTHER INFORMATION: internal primer for tuf gene

<400> SEQUENCE: 9
ctttgatttg accacgttc                                                  19

<210> SEQ ID NO 10
<211> LENGTH: 20
<212> TYPE: DNA
<213> ORGANISM: Artificial
<220> FEATURE:
<223> OTHER INFORMATION: internal primer for tuf gene

<400> SEQUENCE: 10
ttcagtwaca acgcctgatc                                                 20

<210> SEQ ID NO 11
<211> LENGTH: 20
<212> TYPE: DNA
<213> ORGANISM: Artificial
<220> FEATURE:
<223> OTHER INFORMATION: internall primer for tuf gene

<400> SEQUENCE: 11
tggtcgtggt actgttgcta                                                 20

<210> SEQ ID NO 12
<211> LENGTH: 20
<212> TYPE: DNA
<213> ORGANISM: Artificial
<220> FEATURE:
<223> OTHER INFORMATION: internal primer for tuf gene

<400> SEQUENCE: 12
ttcacgtgca ataccacgta                                                 20
```

US 8,445,661 B2

ISOLATED *STAPHYLOCOCCUS PSEUDOLUGDUNENSIS* POLYNUCLEOTIDES

CROSS-REFERENCE TO RELATED APPLICATIONS

This application is a national stage under 35 U.S.C. §371 of International Application PCT/US2007/023637, filed on 9 Nov. 2007, and which is currently expired. International Application PCT/US2007/023637 cites the benefit under 35 U.S.C. §119(e) of the filing date of provisional U.S. Patent Application 60/865,160, filed on 9 Nov. 2006, which is currently expired.

FIELD OF THE INVENTION

The present invention relates to isolated bacteria, and particularly to isolated bacteria of the genus *Staphylococcus*.

BACKGROUND OF THE INVENTION

Staphylococcal species are commonly isolated from blood cultures, and many species are known as important pathogens. *Staphylococcus aureus*, particularly methicillin-resistant *S. aureus* (MRSA), is a virulent pathogen isolated from blood cultures in hospitals around the world (Deresinski, S. (2005) *Clin. Infect. Dis.* 40:562-73.8). *Staphylococcus epidermidis* and other coagulase-negative staphylococci (CoNS) are common members of the normal flora of skin and recognized as frequent contaminants in blood cultures. The incidence of infections caused by CoNS has increased throughout the world, however, making it increasingly more important to identify and differentiate between potentially pathogenic staphylococcal species and possible skin contaminants in a timely manner for a prompt clinical intervention.

One important pathogenic CONS staph species is *Staphylococcus lugdunensis* (Freney, J. et al (1988) *Int. J. Syst. Bacteriol.* 38: 1.68-172). Clinical manifestations of infection with this organism include abscesses, meningitis, ventriculoperitoneal shunt infection, spondylodiscitis, prosthetic joint infection, catheter-related bacteremia, and endocarditis (Castro, J. G., and L. Dowdy (1999) *Clin. Infect. Dis.* 28:681-2; Pareja, J., et al (1998) *Ann. Intern. Med.* 128:603-4; Patel, R. et al (2000) *J. Clin. Microbiol.* 38:4262-3.). The invention provides an isolated biologically pure culture of *Staphylococcus pseudolugdunensis*, a sample of the culture having been deposited as ATCC accession number PT A-7961. The invention also provides an isolated polynucleotide comprising at least about 200 contiguous residues of SEQ ID NO: 1 or of SEQ ID NO: 2, and may also comprise an isolated polynucleotide comprising at least about 300 contiguous residues of SEQ ID NO: 1 or SEQ ID NO: 2, or an isolated polynucleotide comprising at least about 400 contiguous residues of SEQ ID NO: 1 or SEQ ID NO: 2. In some embodiments, misdated polynucleotide comprising at least about 200 contiguous residues of SEQ ID NO: 1 may comprise a polynucleotide comprising residues from nucleotide position 660 to nucleotide position 858. Isolated polynucleotides of the invention may also comprise those that hybridize under moderately stringent conditions to SEQ ID NO: 1 or SEQ ID NO: 2.

Also provided by the invention is a method for distinguishing *Staphylococcus pseudolugdunensis* from *Staphylococcus lugdunensis* isolated from a clinical specimen, or for identifying an unknown bacterial strain from a clinical isolate as *Staphylococcus pseudolugdunensis*, the method comprising comparing the nucleotide sequence of at least 200 contiguous base pairs of SEQ ID NO: 1 with the nucleotide sequence of a corresponding region of the tuf gene sequence of an unknown bacterial strain, wherein the unknown bacterial strain can be determined to be *S. pseudolugdunensis* if it demonstrates an at least about 97% sequence identity, and more preferably at least about 99% sequence identity, with the corresponding at least about 200 base pairs of SEQ ID NO: 1. In one embodiment of a method of the invention, the at least about 200 base pairs of SEQ ID NO: 1 include nucleotide sequences corresponding to contiguous sequences including nucleotide positions 660-858 of SEQ ID NO: 1.

DETAILED DESCRIPTION

The inventors have isolated a previously unknown species of *Staphylococcus*, which they have designated as *Staphylococcus pseudolugdunensis* because it shares certain characteristics with *Staphylococcus lugdunensis*. In contrast to *Staphylococcus lugdunensis*, however, *Staphylococcus pseudolugdunensis* is significantly less pathogenic or generally non-pathogenic.

*Staphylococcus pseudolugdunensis* bacteria are coagulase-negative Gram-positive Staphylococci. They are non-hemolytic, catalase-positive, arginine dihydrolase negative, and more resistant to polymyxin B than to novobiocin. They are not consistent with "*Staphylococcus pettenkoferi*" in terms of their positive ODC reactivity and not consistent with *Staphylococcus pseudolugdunensis* and *Kocuria variansi rosea* in terms of their nucleotide sequence differences in both 16s rRNA and the tuf gene.

During the study period from September 2003 through October, 2005 at Vanderbilt University Hospital, a total of 16 PYR/ODC-positive staphylococcal isolates were recovered from blood cultures. Four of these were further identified based on phenotypic methods as *S. lugdunensis* [2 isolates], S. epidermidis [1 isolate], and S. auricularis [1 isolate] and excluded from this study. The remaining 12 staphylococcal isolates were recovered from 11 patients, with two isolates being recovered from the same patient over a 16-day difference interval. All 12 isolates grew white colonies without hemolysis on blood agar plates. They were clumping factor-negative. Microscopic analysis revealed Gram-positive cocci of 1 μM in diameter in clusters.

Biochemical reaction profiles of these 12 isolates are listed in Table 1. Based on the API STAPH (v4.0) identification system, 8 were originally unidentifiable, having low discrimination scores; 4 were identified as *Kocuria varians/rosea* with identification probabilities ranged from 95.5 to 99.6% (Table 1). All 12 isolates were susceptible to gentamicin, minocycline, rifampin, and vancomycin and had variable susceptibilities to other antibiotics tested (Table 2).

Figure 1:
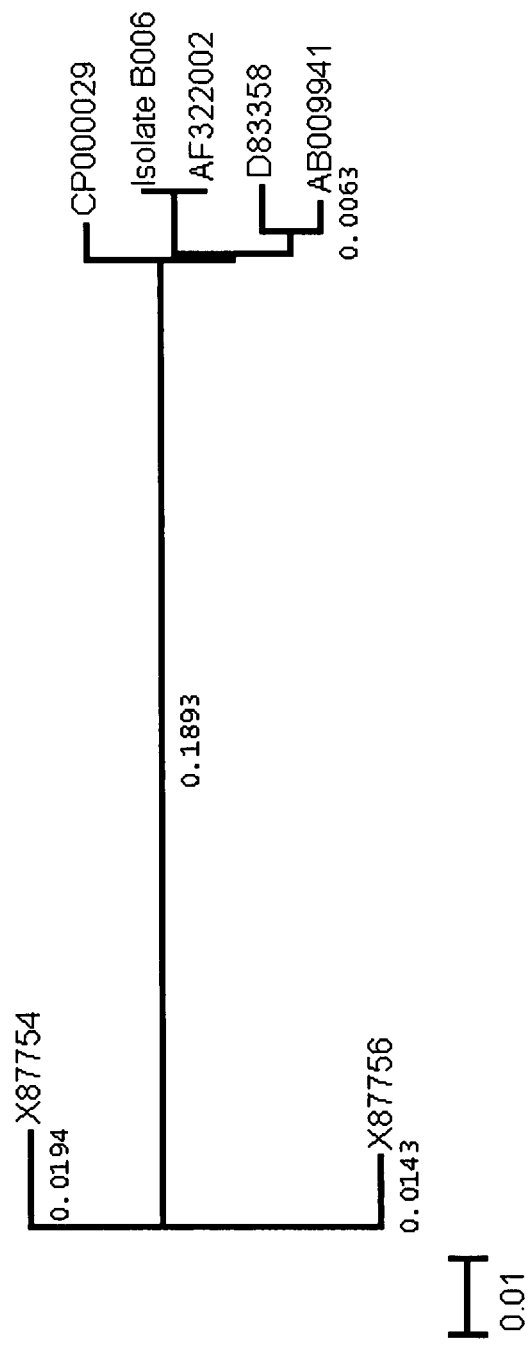
FIG. 1 is a phylogenetic tree illustrating neighbor-joining analysis of the nucleic acid sequences from the prototype isolate B006 with homology to previously published gene sequences of related *Staphylococcus* and *Kocuria* species. Phylogenetic analysis was based on the full 16S rRNA gene sequences. AB009941, AF322002, CP000029, D83358, X87754 and X87756 were *S. lugdunensis*, "*S. pettenkoferi*," *S. epidermidis*, *S. auricularis*, *K. varius* and *K. roseus*, respectively. The scale indicates relative phylogenetic distance.

All 12 isolates possessed an identical partial 16S rRNA gene sequence spanning nucleotide positions 8-539. A full 16S rRNA gene of the prototype strain B006 contained 1556 nucleotides and was closely related to a tentatively assigned "*Staphylococcus pettenkoferi*" (AF322002, Trulzsch, K., et al (2002) *Diagnostic Microbiol. Infect. Dis.* 43:175-82) at 99.94% similarity (FIG. 1). The 16S rRNA gene sequences of the B006 isolate clustered separately from other phenotypically related species with similarities<98%, including *S. lugdunensis* (A13009941, 97.45%), *S. auricularis* (D83358, 97.64%), *S. epidermidis* (CP000029, 97.75%), *Kocuria varians* (X87754, 77.86%) and *Kocuria rosea* (X87756, 78.49%).

Figure 2:
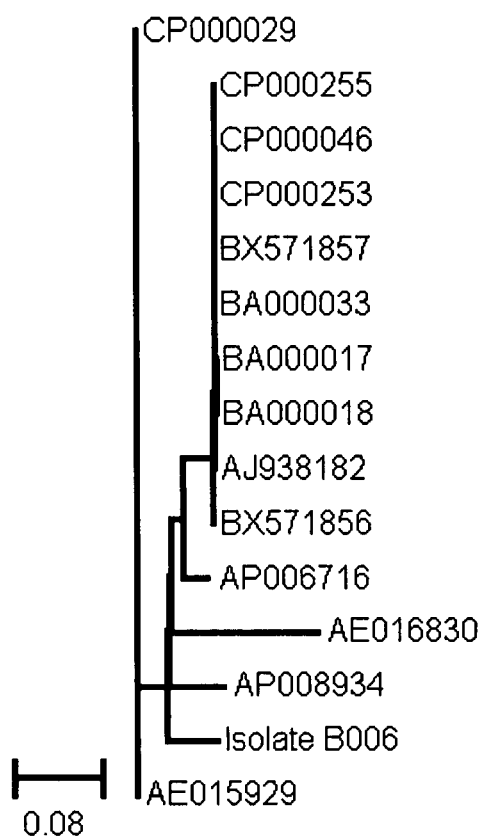
FIG. 2 is a phylogenetic tree illustrating neighbor-joining analysis of the nucleic acid sequences from the prototype isolate B006 with homology to previously published gene sequences of related *Staphylococcus* and *Enterococcus* species. Phylogenetic analysis was based on the full tuf gene sequences. AJ938182, BA000017, BA000018, BA000033, BX571856, BX571857, CP000046, CP000253 and CP000255 are all *S. aureus*. AE015929, AE016830, AP006716, AP008934, and CP000029 were *S. epidermidis*, *E. faecalis*, *S. hemolyticus*, *S. saprophyticus* and *S. epidermidis*, respectively. The scale indicates relative phylogenetic distance.

All 12 isolates also possessed an identical partial tuf gene (200 base pairs) spanning nucleotide positions 660-858, with a difference of 8.6% from that of *S. lugdunensis* (ATCC #700328). The entire tuf gene of the prototype strain B006 contained 1,188 nucleotides and was most closely related to two *S. epidermidis* isolates, RP62A and ATCC 12228, with a similarity of 93.02% (FIG. 2) (Gill, S. R., et al (2005) *J. Bacteriol.* 187: 2426-38; Zhang, Y. Q., et al (2003) *Mol. Microbiol.* 49: 1577-93). These isolates clustered separately from other phenotypically related species, including *S. haemolyticus* (91.59%), *S. aureus* (91.02-91.22%), *S. saprophyticus* (90.35%), and *Enterococcus faecalis* with a similarity of 82.67% (Baba, T., et al (2002) *Lancet* 359:1819-27; Diep, B. A., et al (2006) Lancet 367:731-9; Gill, S. R., et al (2005) *J. Bacteriol.* 187: 2426-38; 15, 18, 19, 24, Zhang, Y. Q., et al (2003) *Mol. Microbiol.* 49:1577-93).

Figure 3:
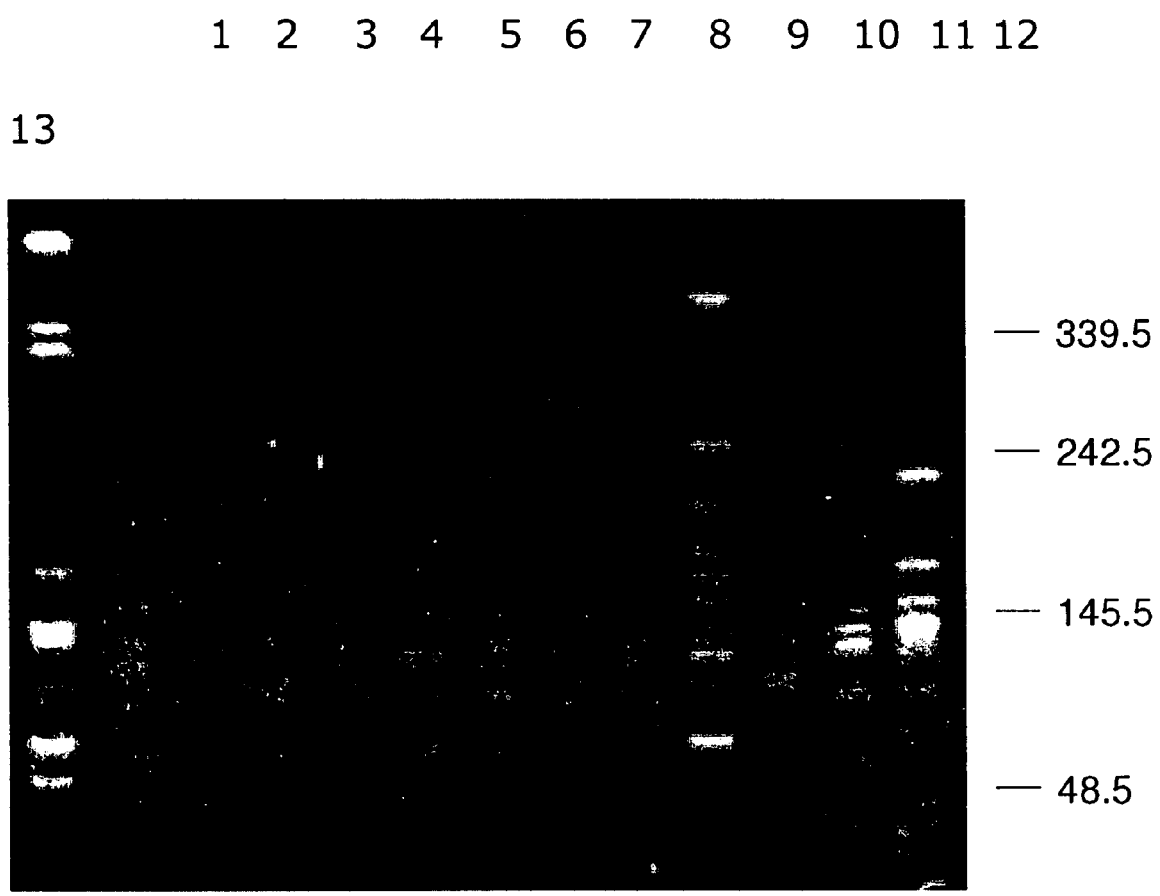
FIG. 3 is a photograph of pulsed-field gel electrophoresis (PFGE) patterns of XbaI-digested genomic DNA of coagulase-negative *Staphylococcus* isolates. Lanes 1 to 13 are isolates of *S. lugdunensis* (ATCC 700328), B006, B230, B060, B333, B277, B287, B292, B334, B354, B715, B739 and B837, respectively. 8230 (lane 3) and B333 (lane 5) are two isolates recovered from the same patient over a 16-day interval. Molecular sizes are expressed in kilobases.

The relatedness of these 12 ODC/PYR-positive CONS was further analyzed by pulsed field gel electrophoresis (PFGE). All isolates were unrelated, except for two isolates (B230 and B333) which were recovered from the same patient over a 16-day interval. These two isolates presented PFGE patterns with a less than 6-band difference, indicating that they are epidemiologically related (FIG. 3). The PFGE data overall indicated that the 12 isolates represent 11 different strains of this species. The patient medical record indicated that the two related isolates had been considered the cause of an intravenous line-associated infection (Table 3). Vancomycin was administered and the line removed. The patient recovered fully.

Medical records of the 11 patients from whom these isolates were recovered were reviewed and the demographic and clinical information are listed in Table 3. Two isolates (B230 and B333), which were recovered from the same patient over a 16-day interval, were considered to be the pathogen that caused an intravenous line-associated infection. The remaining 10 isolates were considered to be contaminants. Antibiotics, including vancomycin, were administered in 6 (54.5%) cases, including one case in which the two isolates were considered pathogens and in 5 of 10 cases in which the isolates were considered contaminants (Table 3).

These 12 new isolates were not consistent with *Staphylococcus pettenkoferi* (Trulzsch, K. H. et al. (2002) *Diagn. Microbiol. Infect. Dis.* 43: 175-182) in terms of their positive ODC reactions, were not consistent with *S. lugdunensis* and *Kocuria varians/rosea* in terms of their nucleotide sequence differences in both the 16S rRNA and the tuf gene. These isolates were determined by the inventors to be similar to most of other CoNS species as skin contaminants of blood cultures and were not differentiated from *S. lugdunensis* based on their biochemical reactions. Based upon the characteristics evidenced by the biochemical reactions, 16S rRNA and tuf gene sequences, as well as the clinical manifestations, the inventors have proposed "*Staphylococcus pseudolugdunensis*" as a novel species of staphylococci, with strain B006 as its prototype. The type strain, B006, was deposited at the American Type Culture Collection (Manassas, Va.), under the Budapest Treaty on the International Recognition of the Deposit of Microorganisms for the Purpose of Patent Procedure, on Nov. 3, 2006 and assigned accession number ATCC PTA-7961.

Of the twelve PYR/ODC-positive staphylococcal isolates recovered from blood cultures, comparative 16S rRNA and tuf gene sequence analysis revealed the isolates to represent a new species within the genus *Staphylococcus*. The new taxon differs from *S. aureus* and most other CoNS species by its positive PYR/ODC reactions. It differs from *S. lugdunensis* by its negative or low acidification of mannose, maltose, lactose, trehalose and N-acetyl-glucosamine, and variable sequences in 16S rRNA and tuf genes.

16S rRNA gene sequence analysis was not sufficiently discriminatory to definitively distinguish certain newly *staphylococcus* strains at the species level, including the *S. pseudolugdunensis* strains identified in the study. The tuf gene, which encodes the elongation factor Tu, is involved in peptide chain formation and is part of the ribosome. These genes are essential constituents of the bacterial genome and are preferred targets for diagnostic purposes. Sequence variations in tuf gene among several CoNS species are sufficient for speciation (Kontos, F., et al (2003) *J. Microbiol. Methods* 55: 465-9, 21). A previous study by others had contrasted three genetic identification methods for identification of CoNS species—16S rRNA, sodA gene and tuf gene sequence comparison—and the results demonstrated tuf gene sequencing to be the most reliable and reproducible method of the three (Heikens, E., et al (2005) *J. Clin. Microbiol.* 43: 2286-90). Based on the full tuf sequence analysis, conservation within a species is quite high (e.g., 99.98% among 9 *S. aureus* strains and 100.0% between 2 *S. epidermidis* strains). In contrast, there is a significant lack of homology or identity between tuf gene sequences of different *Staphylococcus* species. The complete tuf gene sequence of the newly recovered B006 strain demonstrated a sequence identity of 93% in comparison to the nearest match (*S. epidermis*) by phylogenetic analysis. Nucleic acid sequence variation within the tuf gene has been shown by the inventors to provide a reliable means for differentiating between *S. pseudolugdunensis*, *S. lugdunensis*, and other phenotypically-related *Staphylococcus* and *Kocuria* species.

The distribution and natural habitats of this *S. pseudolugdunensis* have not yet been fully determined. Staphylococci are widespread in nature, although they are mainly found living on the skin, skin glands, and mucous membranes of mammals and birds. Staphylococci generally have a benign or symbiotic relationship with their hosts, but may be pathogenic if they gain entry into the host tissue through trauma of the cutaneous barrier, inoculation by needles, or direct implantation of medical devices. Where special care is not taken in obtaining blood specimens, blood contamination by normal skin flora is high. *S. pseudolugdunensis*, like other CoNS species, appear to be part of the normal flora of the human skin surface.

In the inventors' study, of 12 *S. pseudolugdunensis* isolates, 10 were considered to be skin contaminants based on their clinical significance. However, 5 cases (50.0%) received vancomycin and other broad-spectrum antibiotics because they were originally identified as *S. lugdunensis*. Rapid detection and differentiation of *S. pseudolugdunensis* can therefore be critical in the clinical setting in order to limit overuse of broad-range and potentially toxic antibiotics such as vancomycin. Rapid identification-based phenotypic techniques based on double positives in PYR and ODC, when combined with mannose fermentation results, may provide accurate identification. Mannose fermentation, however, requires overnight incubation. Molecular methods, such as a nucleotide probe targeting the tuf gene, can facilitate accurate and rapid identification in a timely manner.

*S. pseudolugdunensis*, as provided by the present invention, comprises a bacterium and its progeny having at least about 97% tuf gene sequence identity to the *S. pseudolugdunensis* strain B006 tuf gene (SEQ. ID NO: 1), and more preferably at least about 97% tuf gene sequence identity to the B006 strain deposited as ATCC PTA-7961. The invention provides an isolated bacterial strain and/or a biologically pure culture of *S. pseudolugdunensis*, *S. pseudolugdunensis* being a pyrrolidonyl arylamidase/ornithine decarboxylase-positive, catalase-positive, coagulase-negative Staphylococcal species represented by the culture deposited with the American Type Culture Collection as ATCC PTA-7961. An isolated bacterial strain is one that has undergone some degree of purification from its natural environment. A culture of a bacterium is considered to be biologically pure if at least about 20% of the bacteria are from one bacterial strain. However, it is preferable if the culture is at least 33% pure, more preferable if the culture is at least 45% pure and most preferable if the culture is at least 90% pure.

The invention also provides isolated polynucleotide (DNA and/or RNA) sequences comprising from at least about 100 to about 1188 base pairs of the sequence of the tuf gene (SEQ NO: 1), and/or at least about 100 to about 1556 base pairs of the sequence of the 16s rRNA (SEQ ID NO: 2) of *S. pseudolugdunensis*. Polynucleotide sequences of the invention include DNA and/or RNA sequences encoding the tuf or 16s rRNA genes and any other amino acids located N-terminal or C-terminal to the gene sequence. It is to be understood that nucleic acid sequences may include additional residues either 5' or 3' to the polynucleotide of SEQ ID NO: 1 or SEQ ID NO: 2. A nucleic acid fragment of almost any length may be employed, and may be combined with other DNA sequences, such as promoters, polyadenylation signals, additional restriction enzyme sites, multiple cloning sites, other coding segments, and the like. Therefore, overall length may vary considerably.

The invention also provides a method for identifying *S. pseudolugdunensis* from clinical isolates, the method comprising sequencing all or at least about 200 base pairs of the tuf gene of an unknown bacterial strain and comparing that sequence with a corresponding region of SEQ ID NO: 1 to determine the percentage of sequence identity between the unknown and the reference strain B006, wherein *S. pseudolugdunensis* species may be identified as having at least about 97%, and more preferably at least about 99%, sequence similarity or sequence identity to a corresponding region of SEQ ID NO: 1.

Alternatively, a method for identifying *S. pseudolugdunensis* may comprise isolating a polynucleotide comprising at least about 200 residues of the tuf gene of an unknown bacterial isolate and hybridizing the polynucleotide to a polynucleotide comprising SEQ ID NO: 1 under moderately stringent conditions, moderately stringent hybridization conditions being known to those of skill in the art of molecular biology. For example, moderately stringent hybridization may be performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about 5×10 cpm/µg), while the washes are performed at about 50° C. with a wash solution containing 2×SSC and 0.1% sodium dodecyl sulfate. Hybridization may involve a polynucleotide comprising DNA, RNA; sense, or antisense. All, or a portion of at least about 200 bp of SEQ ID NO: 1 may also be used as a molecular diagnostic probe for use in a variety of hybridization and other test methods for microbial identification from clinical isolates, those methods being known to those of skill in the art of microbial identification.

EXAMPLES

Twelve staphylococcal isolates from blood cultures were characterized, each pyrrolidonyl arylamidase/ornithine decarboxylase-positive but not recognized by a *S. lugdunensis*-specific primer/probe set targeting the tuf gene (which encodes the translation elongation factor Tu (Heikens, E., et al (2005) *J. Clin. Microbiol.* 43: 2286-90; Kontos, F., et al (2003) *J. Microbiol. Methods* 55: 465-9; Martineau, F., et al (2001) *J. Clin. Microbiol.* 39: 2541-7.). These isolates cannot be definitively differentiated from other common clinically encountered staphylococci based on biochemical reactions including those used in the API STAPH identification system (Brun, Y., et al (1990) *J. Clin. Microbiol.* 8: 503-8; 5; Gemmell, C. G., and J. E. Dawson (1982) *J. Clin. Microbiol.* 16: 874-7; Layer, F., B. et al (2006) *J. Clin. Microbiol.* 44: 2824-30). Clinically, these isolates behaved mainly as skin contaminants except for two isolate; which were recovered from the same patient, with a central line-associated infection, over a 16-day interval. A serial genetic analysis including 16S rRNA and elongation factor Tu (tuf) gene sequence analysis indicates that these isolates are new staphylococcal species and the inventors have proposed the designation of *S. pseudolugdunensis* sp. nov.

Bacterial Isolates and Reference Strains

PYR and ODC dual-positive *staphylococcus* isolates recovered by a BACTEC® 9240 blood culture system (Becton Dickinson Diagnostic Instrument Systems, Sparks, Md.) from September 2003 through October, 2005 at Vanderbilt University Hospital were included in the study. Two related reference strains were obtained from the American Type Culture Collection (ATCC, Manassas, Va.) including *S. aureus* (ATCC #35556), and *S. lugdunensis* (#700328). Clinical isolates and ATCC strains were collected and saved in brain heart infusion (BHI) containing 7.5% glycerol at −80° C. for further study.

Phenotypic Identification

Both clinical isolates and reference isolates were first identified by the conventional method based on colony size and pigment; anaerobic and aerobic growth; the presence of clumping factor, Staphaurex latex agglutination (Murex Diagnostics Inc., Norcross, Ga.), hemolysins, oxidase, ODC, urease, and PYR (De Paulis, A. N., et al (2003) *J. Clin. Microbiol.* 41: 1219-24, 16, 25, 33). Species identification further confirmed by using an API STAPH (bioMerieux Vitek, Inc., Hazelwood, Mo.) according to the manufacturer's instructions (Brun, Y., et al (1990) *J. Clin. Microbiol.* 8: 503-8; Chapin, K., and M. Musgnug (2003) *J. Clin. Microbiol.* 41: 4324-7; Gemmell, C. G., and J. E. Dawson (1982) *J. Clin. Microbiol.* 16:874-7; Heikens, B., et al (2005) *J. Clin. Microbiol.* 43: 2286-90; Layer, F., B. et al (2006) *J. Clin. Microbiol.* 44: 282430.). PYR and ODC were performed with *S. aureus* (ATCC #25923) and *S. lugdunensis* (ATCC #700328) included as negative and positive controls, respectively. Biochemical tests included acid production from D-glucose, D-trehalose, D-mannitol, D-mannose, xylose, maltose, lactose, sucrose, N-acetylglucosamine, raffinose, D-fructose, D-melibiose, xylitol, and α-methyl-glucosamine; nitrate reduction; and alkaline phosphatase, arginine dihydrolase, urease, and acetoin production. Supplementary tests were performed as suggested by the kit instructions (Chapin, K., and M. Musgnug (2003) *J. Clin. Microbiol.* 41:4324-7; Layer, F., et al (2006) *J. Clin. Microbiol.* 44:2824-30.). Biochemical reactions, including catalase, coagulase, D-glucose, D-mannitol, D-fructose, galactose, lactose, maltose, sucrose, D-trehalose, xylose, nitrate reduction, arginine dihydrolase, urease, and novobiocin and polymyxin B resistance, were further confirmed at the Tennessee Department of Health Laboratory Services in Nashville, Tenn., using phenotypic methods recommended by the United States Centers for Disease Control (CDC), Atlanta, Ga. (Kloose, W. E. and T. L. Bannerman (1995) *Staphylococcus and Micrococcus*, p. 282-298, in P. R. Murray et al. (eds.) *Manual of Clinical Microbiology*, 6th ed., American Society for Microbiology Press, Washington, D.C.; Kloose, W. E. and K. H. Schleifer (1975) *J. Clin. Microbiol.* 1: 82-88).

Antimicrobial Susceptibility Testing

In vitro antimicrobial susceptibility testing for amoxicillin-clavulanate, cefazolin, clindamycin, erythromycin, gentamicin, levofloxacin, minocycline, penicillin, rifampin, trimethoprim/sulfamethoxazole (SXT) and vancomycin was determined by a disc diffusion method in accordance with Clinical and Laboratory Standards Institute guidelines (CLSI Performance standards for antimicrobial disk susceptibility tests; Approved standard, 9th ed. (2006) Clinical and Laboratory Standards Institute, Wayne, Pa.).

16S rRNA Gene Amplification and Sequencing

A loopful of each purified bacterial isolate was put into 1 ml of distilled water. The suspension was vortexed, heated for 7 min at 95° C., centrifuged at 8,000×g for 15 s, and 1 µl of supernatant was used for PCR amplification. A highly conserved primer set (5'-TGG AGA GTT TGA TCC TGG CTC AG-3' and 5'-AAG GAG GTG ATC CAR CCG CA-3'; R=G or A; SEQ ID NOS: 3 and 4, respectively) spanning nucleotide positions 5-1,553 of the 16S rRNA gene was used to amplify the DNA fragment by PCR (Tang, Y. W., et al (1998) *Clin. Infect. Dis.* 26:389-92.). Partial or full 16S rRNA gene sequences were determined bi-directionally using the PCR primers and/or several additional internal primers on an ABI PRISM 3730 DNA sequencer (Applied Biosystems, Foster City, Calif.) as previously described (Tang, Y. W., et al (1998) *J. Clin. Microbiol.* 36:3674-9; Tang, Y. W., et al (2000) *J. Clin. Microbiol.* 38:1676-8).

tuf Gene Amplification and Sequencing

Full tuf sequences of 13 staphylococcal species (9 *S. aureus*, 2 *S. epidermidis*, 1 *S. haemolyticus*, and 1*S. saprophyticus*) available in the GenBank were retrieved and aligned (Baba, T., et al (2002) *Lancet* 359:1819-27; Diep, B. A. et al (2006) *Lancet* 367:731-9; Gill, S. R., et al (2005) *J. Bacteriol.* 187:2426-38; Holden, M. T., et al (2004) *Proc. Natl. Acad. Sci. USA* 101:9786-91; Kuroda, M., et al (2001) *Lancet* 357:1225-40; Kuroda, M., A. et al (2005) *Proc. Natl. Acad. Sci. USA* 102:33272-7; Takeuchi, F., et al (2005) *J. Bacteriol.* 187:7292-308; Zhang, Y. Q., et al (2003) *Mol. Microbiol.* 49:1577-93.). A degenerate primer set (5'-TAA GAA TAG GAG AGA TTT WAT AAT G-3' and 5'-AAA TTA TTC AAA GAT TWC WGT-3', W=A or T; SEQ ID NOS: 5 and 6, respectively) was designed to amplify the entire tuf gene of the first/prototype isolate B006 by PCR. The PCR amplification product was sequenced bi-directionally using four internal primers (5'-AGA ATA GGA GAG ATT TWA TAA TGG-3', 5'-TCT GAC AAA CCA TTC ATG AT-3', 5'-CTT TGA TTT GAC CAC GTT C-3', and 5'-TTC AGT WAC AAC GCC TGA TC-3'; SEQ ID NOS: 7-10, respectively) on an ABI PRISM 3730 DNA sequencer (Applied Biosystems, Foster City, Calif.). A partial tuf gene spanning nucleotide positions 666-858 (Martineau, F., et al (2001) *J. Clin. Microbiol.* 39:2541-7) was amplified for all isolates by using a conserved primer set (tuf-f, 5'-TGG TCG TGG TAC TGT TGC TA-3'; tuf-r, 5'-TTC ACG TGC AAT ACC ACG TA-3'; SEQ ID NOS: 11 and 12, respectively). The same amplification primers were used for determining partial tuf gene sequence.

Phylogenetic Analysis

Sequence homology searches were performed through BLAST queries of GenBank, the Ribosomal Database Project II site (http://rdp.cme.msu.edu/html/index.html) and the MicroSeq Database Library (Applied Biosystems, Foster City, Calif.) as previously described (Tang, Y. W., et al (1998) *J. Clin. Microbiol.* 36: 3674-9; Tang, Y. W., et al (2000) *J. Clin. Microbiol.* 38:1676-8). Phylogenetic analysis using neighbor joining was performed by using DS Gene software (version 1.5, Accelrys Inc., San Diego, Calif.)

Nucleotide Sequence Accession Numbers and Strain Depositions

Partial or full 16S rRNA gene and tuf gene sequences were deposited in the GenBank database as AY560519, DQ117531, and DQ117530, respectively. The type strain (B8006) of *S. pseudolugdunensis* was isolated from the blood of a 48-year-old man in Nashville, Tenn. It was deposited under the terms of the Budapest Treaty with the American Type Culture Collection, Manassas, Va., on Nov. 3, 2006 under accession number ATCC PTA-7961.

TABLE 1

Biochemical characteristics and antimicrobial susceptibility profiles of 12 unusual isolates and related species

| | Unknowns (n = 12) | | | | | | | | | | | | |
|---|---|---|---|---|---|---|---|---|---|---|---|---|---|
| | B006 | B060 | B292 | B230 | B333 | B334 | B354 | B277 | B837 | B739 | B287 | B715 | Summary |
| Phenotype: | | | | | | | | | | | | | |
| Ornithine decarboxylase (ODC) | + | + | + | + | + | + | + | + | + | + | + | + | 100 |
| Pyrrolidonyl arylamidase (PYR) | + | + | + | + | + | + | + | + | + | + | + | + | 100 |

TABLE 1-continued

Biochemical characteristics and antimicrobial susceptibility profiles of 12 unusual isolates and related species

| | B006 | B060 | 13292 | B230 | B333 | B334 | B354 | 8277 | B837 | 8739 | 8287 | 13715 | % |
|---|---|---|---|---|---|---|---|---|---|---|---|---|---|
| Arginine dihydrolase (ADH) | − | − | − | − | − | − | − | − | − | − | − | − | 0 |
| Catalase (CAT) | + | + | + | + | + | + | + | + | + | + | + | + | 100 |
| Coagulase (COA) | − | − | − | − | − | − | − | − | − | − | − | − | 0 |
| Urease (URE) | + | − | + | + | + | + | + | + | + | + | − | + | 83 |
| Nitrate reduction (NIT) | + | + | + | + | − | − | − | + | + | + | + | + | 75 |
| Alkaline phosphatase (PAL) | + | + | − | + | + | − | + | − | − | + | + | + | 67 |
| Voges-Proskauer (VP) | + | − | − | + | + | + | − | − | − | + | + | + | 58 |
| Acidification: | | | | | | | | | | | | | |
| D-glucose (GLU) | + | + | + | + | + | + | + | + | + | + | + | + | 100 |
| D-fructose (FRU) | + | + | + | + | + | + | + | + | + | + | + | + | 100 |
| D-mannose (MNE) | − | − | − | − | + | − | − | − | − | − | − | − | 8 |
| D-maltose (MAL) | − | − | − | − | + | − | − | − | − | − | − | − | 8 |
| D-lactose (LAC) | − | − | − | − | − | + | − | + | + | + | − | − | 33 |
| D-trehalose (TRE) | + | + | + | + | + | + | + | + | + | + | + | + | 100 |
| D-mannitol (MAN) | + | − | + | − | − | + | − | + | + | + | − | − | 50 |
| D-raffinose (RAF) | − | − | − | − | − | − | − | − | − | − | − | − | 0 |
| D-xylose (XYL) | − | − | − | + | + | + | + | + | + | − | − | − | 50 |
| Galactose (GAL) | − | − | − | − | − | − | − | − | − | − | − | − | 0 |
| Sucrose (SAC) | + | + | + | − | + | + | + | + | + | + | + | + | 92 |
| Xylitol (XLT) | − | − | − | − | − | − | − | − | − | − | − | − | 0 |
| D-melibiose (MEL) | − | − | − | − | − | − | − | − | − | − | − | − | 0 |
| D-glycopyranoside (MDG) | − | − | − | − | − | − | − | − | − | − | − | − | 0 |
| N-acetyl-glucosamine (NAG) | − | − | − | − | − | − | − | − | − | − | − | − | 0 |
| Resistance/Susceptibility: | | | | | | | | | | | | | |
| Novobiocin (NOV) | I | I | R | I | I | R | I | R | R | I | R | I | 42 |
| Polymyxin B (POL) | S | S | S | S | I | S | S | I | R | S | S | S | 8 |

| | S. lugdunensis | S. epidermidis | S. auricularis | K. varians/rosea | "S. pettenkoferi"[b] |
|---|---|---|---|---|---|
| Phenotype: | | | | | |
| Ornithine decarboxylase (ODC) | + | v | + | ND | − |
| Pyrrolidonyl arylamidase (PYR) | + | − | v | ND | + |
| Arginine dihydrolase (ADH) | 1 | 73 | 90 | 1 | − |
| Catalase (CAT) | + | + | + | + | + |
| Coagulase (COA) | − | − | − | − | − |
| Urease (URE) | 50 | 88 | 1 | 29 | +/− |
| Nitrate reduction (NIT) | 99 | 80 | 81 | 75 | + |
| Alkaline phosphatase (PAL) | 16 | 84 | 0 | 4 | − |
| Voges-Proskauer (VP) | 99 | 68 | 1 | 8 | ND |
| Acidification: | | | | | |
| D-glucose (GLU) | 100 | 100 | 100 | 91 | + |
| D-fructose (FRU) | 89 | 99 | 99 | 92 | + |
| D-mannose (MNE) | 88 | 70 | 36 | 8 | +/− |
| D-maltose (MAL) | 99 | 99 | 72 | 1 | − |
| D-lactose (LAC) | 66 | 81 | 10 | 1 | − |
| D-trehalose (TRE) | 99 | 2 | 90 | 8 | +/− |
| D-mannitol (MAN) | 0 | 0 | 9 | 1 | +/− |
| D-raffinose (RAF) | 0 | 1 | 0 | 4 | − |
| D-xylose (XYL) | 0 | 1 | 0 | 8 | − |
| Galactose (GAL) | 0 | 0 | 0 | 0 | − |
| Sucrose (SAC) | 100 | 94 | 40 | 4 | + |
| Xylitol (XLT) | 0 | 0 | 0 | 0 | − |
| D-melibiose (MEL) | 0 | 1 | 0 | 0 | − |
| D-glycopyranoside (MDG) | 0 | 4 | 0 | 0 | ND |
| N-acetyl-glucosamine (NAG) | 90 | 18 | 15 | 1 | − |
| Resistance/Susceptibility: | | | | | |
| Novobiocin (NOV) | S | S | S | ND | S |
| Polymyxin B (POL) | v | R | S | ND | ND |

[a]Indexes used:: "+", positive; "−", negative; "v", variable; ND, not done; "R", resistant; "S", susceptible. Numbers are positive percentage of a panel of isolates based on API STAPH results or resistance percentage in antimicrobial susceptibility profiles.
[b]Trulzsch, K. H. et al. (2002), "*Staphylococcus pettenkoferi*," a novel staphylococcal species isolated from clinical specimens." *Diagn Microbiol. Infect. Dis.* 43: 175-82.

TABLE 2

Antimicrobial Susceptibility Profiles of 12 Unusual Isolates and Related Species

| | B006 | B060 | 13292 | B230 | B333 | B334 | B354 | 8277 | B837 | 8739 | 8287 | 13715 |
|---|---|---|---|---|---|---|---|---|---|---|---|---|
| Amoxicillin-clavulanate | R | S | S | S | S | R | S | S | R | R | S | R |
| Cefazolin | R | S | S | S | S | R | S | S | R | R | S | R |

TABLE 2-continued

Antimicrobial Susceptibility Profiles of 12 Unusual Isolates and Related Species

|  | B006 | B060 | 13292 | B230 | B333 | B334 | B354 | 8277 | B837 | 8739 | 8287 | 13715 |
|---|---|---|---|---|---|---|---|---|---|---|---|---|
| Clindamycin | S | S | S | S | R | R | S | S | R | R | S | S |
| Erythromycin | R | S | S | S | R | R | S | S | R | R | S | S |
| Gentamicin | S | S | S | S | S | S | S | S | S | S | S | S |
| Levofloxacin | S | S | S | R | S | R | S | S | S | S | R | R |
| Methicillin | R | S | S | S | S | R | S | S | R | R | S | R |
| Minocycline | S | S | S | S | S | S | S | S | S | S | S | S |
| Penicillin | R | R | R | R | R | R | S | S | R | R | R | R |
| Rifampin | S | S | S | S | S | S | S | S | S | S | S | S |
| Trimethoprim/sulfamethoxazole | S | R | S | R | S | R | S | S | S | S | R | R |
| Vancomycin | S | S | S | S | S | S | S | S | S | S | S | S |

R—resistant;

S—susceptible

TABLE 3

Demographic and clinical information of 11 patients from who the 12 unusual isolates were recovered

| Case/Isolate | Sex | Age | Clinical presentation | Outcome at discharge | ID consult | Therapy specific for the isolate | Clinical significance |
|---|---|---|---|---|---|---|---|
| B006 | M | 48 | Large R MCA territory infarction | Stable | No | No | Contaminant |
| B060 | F | 55 | Aspiration pneumonia | Recovered | No | Vancomycin | Contaminant |
| B230/B333[a] | M | 67 | Intravenous line-associated infection | Recovered | No | Vancomycin, line pulled | Pathogen |
| B277 | F | 94 | Left lower lobar pneumonia, UTI | Stable | No | No | Contaminant |
| B287 | F | 78 | UTI with altered mental status | Recovered | No | No | Contaminant |
| B292[b] | M | 30 | Chronic myeloid leukemia, blast crisis | Stable | Yes | Vancomycin | Contaminant |
| B334 | F | 72 | Multiple substance overdose with respiratory failure | Recovered | No | No | Contaminant |
| B354 | M | 37 | Traumatic injury to lumbosacral spine | Stable | Yes | Vancomycin | Contaminant |
| B715[c] | M | 81 | UTI with Alzheimer's dementia | Recovered | No | No | Contaminant |
| B739 | M | 37 | Pyomyositis of right posterior thigh, cultures of thigh revealed no growth | Stable | No | Vancomycin | Contaminant |
| B837 | F | 65 | AMS with renal failure | Stable | Yes | Vancomycin | Contaminant |

[a]These two isolates were recovered from the same patient over a 16-day interval.

[b]Later determined to have a pulmonary fungal infection.

[c]Second CoNS (S. epidermidis) was recovered from the same blood culture specimen.

What is claimed is:

1. An isolated polynucleotide comprising at least 200 contiguous residues of SEQ ID NO: 1.

2. The isolated polynucleotide of claim 1 comprising at least 300 contiguous residues of SEQ ID NO: 1.

3. The isolated polynucleotide of claim 1 comprising at least 400 contiguous residues of SEQ ID NO: 1.

4. An isolated polynucleotide of claim 1 wherein the at least about 200 contiguous residues of SEQ ID NO: 1 comprise residues 660 to 858.

* * * * *